United States Patent [19]
Ohsaki et al.

[11] Patent Number: 5,838,453
[45] Date of Patent: Nov. 17, 1998

[54] APPARATUS AND METHOD FOR MEASURING OPTICAL ANISOTROPY

[75] Inventors: Yoshinori Ohsaki, Machida; Takashi Suzuki, Yokohama, both of Japan

[73] Assignee: Canon Kabushiki Kaisha, Tokyo, Japan

[21] Appl. No.: 590,814

[22] Filed: Jan. 24, 1996

[30] Foreign Application Priority Data

Jan. 27, 1995 [JP] Japan .................................. 7-012103
Jan. 27, 1995 [JP] Japan .................................. 7-012104
Aug. 9, 1995 [JP] Japan .................................. 7-203385

[51] Int. Cl.$^6$ .............................. G01N 21/55; G01J 4/00
[52] U.S. Cl. .......................................... 356/445; 356/369
[58] Field of Search ...................... 356/445, 369

[56] References Cited

U.S. PATENT DOCUMENTS

| | | | |
|---|---|---|---|
| 4,516,855 | 5/1985 | Korth | 356/369 |
| 4,997,278 | 3/1991 | Finlan et al. | 356/445 |
| 5,108,185 | 4/1992 | Mansuripur et al. | 356/369 |

FOREIGN PATENT DOCUMENTS

| | | |
|---|---|---|
| 0 575 132 | 12/1993 | European Pat. Off. |
| 42 11 467 | 10/1993 | Germany . |
| 6-34530 | 2/1994 | Japan . |
| 989403 | 1/1983 | U.S.S.R. |

OTHER PUBLICATIONS

Takezoe, H., et al., "Experimental Studies on Reflection Spectra in Monodomain Cholesteric Liquid Crystal Cells: Total Reflection, Subsidiary Oscillation and Its Beat or Swell Structure," Japanese Journal of Applied Physics, vol. 22, No. 7, pp. 1080–1091 (Jul. 1983).

Yamashita, M., "Dependence of Temporal Behavior of Conoscopic Figures in Nematic Liquid Crystals on Film Thickness," Japanese Journal of Applied Physics, vol. 25. No. 1, pp. 1–7 (Jan. 1986).

Xue, J., et al. "Surface Orientation Transitions in Surface Stabilized Ferroelectric Liquid Crystal Structures," Applied Physics Lett. 53 (24) pp. 2397–2399 (Dec. 1988).

Hinov, H.P., et al., "Total Internal Reflection from Nematic Liquid Crystals," Revue Phys. Appl. 15, pp. 1307–1321 (Aug. 1980).

*Primary Examiner*—Frank G. Font
*Assistant Examiner*—Amanda Merlino
*Attorney, Agent, or Firm*—Fitzpatrick, Cella, Harper & Scinto

[57] ABSTRACT

An apparatus for measuring an optical anisotropy of an object to be examined, such as a liquid crystal, based on an interaction of an evanescent wave occurring during total reflection of a beam with the object is disclosed. The apparatus includes a transparent member having a curved surface and a flat surface for mounting an object to be examined thereon; a light source disposed opposite to a first region of the curved surface of the transparent member so as to emit a beam incident through the first region and the transparent member to an outer surface of the object; a polarizer disposed on the emission side of the light source; an incident optical system disposed between the light source and the first region of the curved surface; a photodetector disposed opposite to a second region of the curved surface of the transparent member so as to detect a beam emitted from the light source, totally reflected at a proximity of the outer surface of the object and incident thereto through the second region; and an analyzer disposed between the photodetector and the second region of the curved surface. The object to be examined may be mounted movably on the flat surface of the transparent member via a liquid having a refractive index almost equal to that of the transparent member.

44 Claims, 7 Drawing Sheets

APPARATUS AND METHOD FOR MEASURING OPTICAL ANISOTROPY

FIELD OF THE INVENTION

The present invention relates to an apparatus and a method for measuring the optical anisotropy of a substance. More particularly, the present invention relates to an apparatus and a method for measuring an optical anisotropy of a liquid crystal in order to determine a pretilt angle of the liquid crystal, and a process for producing a liquid crystal device by using the optical anisotropy measurement apparatus.

DESCRIPTION OF THE RELATED ART

In production of a liquid crystal device, a treatment for aligning liquid crystal molecules such as rubbing has been generally performed. By the aligning treatment, liquid crystal molecules are aligned to form a certain angle (called a pretilt angle), with respect to a substrate surface in a liquid crystal device. The magnitude of the pretilt angle and a fluctuation thereof in a liquid crystal device are one of major factors determining the optical performance of the liquid crystal device. Further, in contrast with a solid-state crystal, a liquid crystal is liable to result in more or less locally different pretilt angles. It is generally preferred, however, that the pretilt angle is uniform in a liquid crystal device. Accordingly, the measurement of a pretilt angle of a liquid crystal and a deviation or distribution thereof in a liquid crystal device is important in development and production control of liquid crystal devices.

Figure 12:
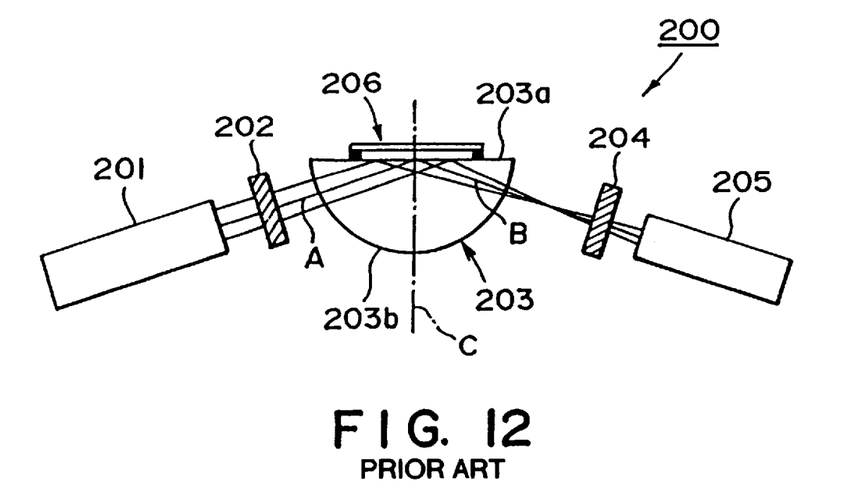
FIG. 12 is a schematic illustration of a conventional optical anisotropy measurement apparatus.

For the above reason, there has been widely known a method of measuring an optical anisotropy of a liquid crystal to calculate a pretilt angle in a liquid crystal device, e.g., by using a total reflection-type optical anisotropy measurement apparatus as shown in FIG. 12.

Referring to FIG. 12, an optical anisotropy measurement apparatus 200 includes a He—Ne laser 201, a polarizer 202, a spherical glass 203 (e.g., a hemispherical glass having a diameter of 20–30 mm and a refractive index of ca. 1.9), an analyzer 204 and a photodetector 205 so that a liquid crystal cell 206 for measurement is integrally formed with a flat surface 203a of the spherical segment glass 203.

Figure 13:
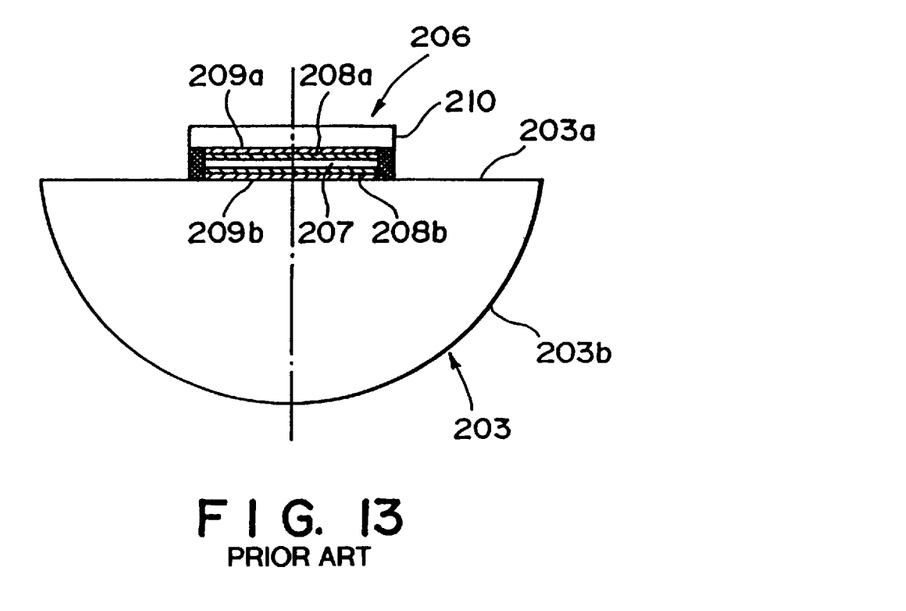
FIG. 13 is a partial enlarged illustration thereof.

As shown in FIG. 13, the liquid crystal cell 206 is disposed to include the spherical segment lens 203 having thereon a transparent electrode 209b (of, e.g., a ca. 0.1 $\mu$m-thick ITO (indium-tin-oxide) film having a refractive index of ca. 1.95) contacting the flat surface 203a and an alignment film 208b (of, e.g., a ca. 0.02 $\mu$m-thick polyimide film having a refractive index of ca. 1.6), and also a glass substrate 210 similarly having thereon a transparent electrode 209a and an alignment film 208a so that the alignment films are disposed on the inner sides to sandwich a liquid crystal layer 207 therebetween. The flat surface 203a and the glass substrate 210 are bonded to each other with a sealant surrounding the liquid crystal layer 207. In other words, the spherical segment glass 203 functions as one substrate constituting the liquid crystal cell 206.

The spherical segment glass 203 preferably has a shape of a hemisphere or a shape close thereto, and a curvature center in the measurement region or a region close thereto.

The spherical segment glass 203 integrally forming a part of the liquid crystal cell 206 is rotatably supported so that it can rotate about a rotation axis C perpendicular to the flat surface 203a thereof.

On one side (left side in FIG. 12) of the spherical segment glass 203, the He—Ne laser (light source) 201 is disposed so as to emit incident light flux A (laser beam, parallel light flux) incident to the flat surface 203a from a lower oblique direction. On the other side of the spherical segment glass 203, the photodetector 205 is disposed to detect an outgoing beam B emitted through the spherical surface 203b after total reflection at a boundary between the alignment film 208b and the transparent electrode 209b. Further, the polarizer 202 is disposed between the He—Ne laser 201 and the spherical segment glass 203 so as to convert the beam A from the He—Ne laser into linearly polarized light, and the analyzer 204 is disposed between the spherical segment glass 203 and the photodetector 205 so as to have a polarization direction perpendicular to that of the analyzer 202.

By using the above-mentioned conventional optical anisotropy measurement apparatus 200, the optical anisotropy measurement has been performed in the following manner.

Incident beam (parallel light flux) A passes through the polarizer 202 to be converted into linearly polarized light and then enters the spherical segment glass 203 through the spherical surface 203a thereof. The incident beam A having entered the spherical segment glass 203 is slightly converged by the power of the spherical segment glass 203 and then totally reflected at the boundary between the alignment film 208b and the transparent electrode 209b. The total reflection is caused by a difference in refractive index between the alignment film 208b and the transparent electrode 209b (the refractive index of the alignment film 208b being smaller than that of the transparent electrode 209b).

During the total reflection, an evanescent wave occurs and enters the alignment film 208b. The evanescent wave proceeds for only a small distance in a direction perpendicular to the boundary. However, as the alignment film 208b is very thin (ca. 0.02 $\mu$m in thickness), the evanescent wave can enter the liquid crystal layer 207 and interact with liquid crystal molecules proximate to the boundary between the liquid crystal layer 207 and the alignment film 208b, returns into the spherical segment glass 203 and is emitted together with the totally reflected light as an outgoing beam B through the spherical surface 203b of the spherical segment glass 203.

The outgoing beam B emitted from the spherical segment glass 203 is once converged and passes through the analyzer 204 having a polarization direction perpendicular to that of the polarizer 202, whereby only a polarized light component having a polarization direction perpendicular to that of the incident beam A is allowed to reach the photodetector 205.

Figure 14:
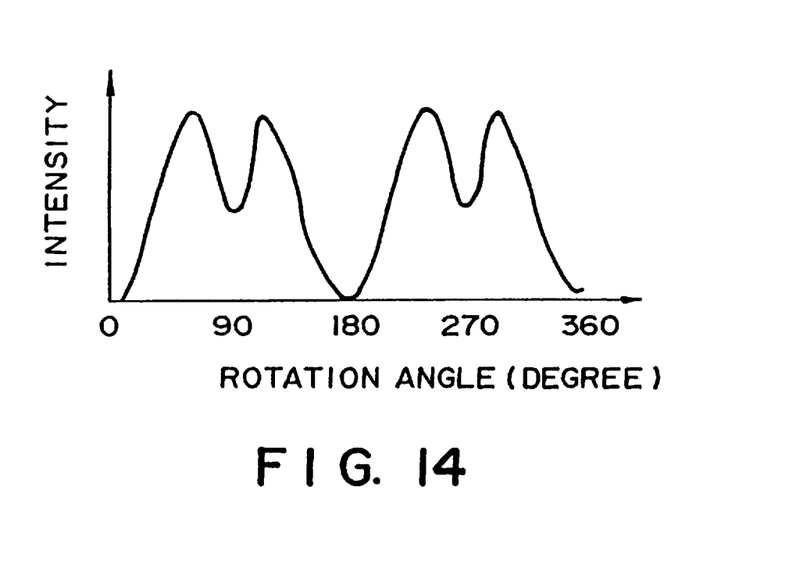
FIG. 14 is a graph showing an example of measured optical anisotropy pattern obtained by using such an optical anisotropy measurement apparatus.

When the spherical segment glass 203 is rotated about the rotation axis C, the director of liquid crystal molecules (which is a unit vector representing the orientation direction of liquid crystal molecules) in the liquid crystal layer 207 is changed relative to the electric field direction of the laser beam A incident to the spherical segment glass 203. Accordingly, corresponding to the rotation angle of the spherical segment glass 203 (i.e., that of the liquid crystal cell 206), the polarization state of the outgoing beam B emitted from the spherical segment glass is changed. By plotting the outputs of the photodetector 205 corresponding to the rotation angles of the spherical segment glass 203 (=the rotation angle of the liquid crystal cell 206), a characteristic curve as shown in FIG. 14 representing the optical anisotropy of the liquid crystal is obtained, and a pretilt angle can be calculated from the characteristic curve.

As described above, the optical anisotropy measurement apparatus 200 allows the measurement of the optical anisotropy of a liquid crystal based on a change in polarization state of the outgoing beam B corresponding to the interaction of the evanescent wave caused at the time of total reflection with liquid crystal molecules, and allows the determination of a pretilt angle based on the optical anisotropy. Based on the property of the evanescent wave that it reaches only a narrow region from the boundary, the optical anisotropy of the liquid crystal in proximity to the boundary between the liquid crystal layer 207 and the alignment film 209b is measured.

By the optical anisotropy measurement method, the optical anisotropy in proximity to a boundary of an objective material other than a liquid crystal can also be measured. For example, the optical anisotropy in proximity to a boundary of a plastic product obtained by compression molding can be measured similarly.

The above-mentioned optical anisotropy measurement apparatus 200 is accompanied with a problem that the incident beam A entering the measurement region is governed by the characteristics of the He—Ne laser 201 and the spherical segment glass 203.

More specifically, in the optical anisotropy measurement apparatus 200, the incident beam A entering the spherical segment glass 203 is slightly converged due to the power of the spherical segment glass, so that the incident beam A is caused to have a somewhat broadened incident angle at the boundary between the alignment film 208b and the transparent electrode 209b, thereby resulting in a somewhat inferior measurement accuracy.

Further, an ordinary liquid crystal device used for display, etc., may comprise several hundreds of thousand to several million minute pixels, each having a square size on the order of several tens to several hundreds $\mu$m square. In a liquid crystal device different from a crystal, a total irregularity, such as locally different pretilt angles, is liable to occur. For example, in production of an active matrix-type liquid crystal device, the substrates are subjected to rubbing with a cloth comprising fiber of ca. 20 $\mu$m in diameter after patterning the electrodes thereon for partitioning the pixels, so that an alignment irregularity is liable to occur in one pixel or between adjacent pixels. Accordingly, for evaluation and development of such liquid crystal devices, it is important to evaluate a pretilt angle in a minute region of several $\mu$m to several tens $\mu$m in diameter and compare it with a designed value. Not only in such an active matrix-type liquid crystal device but also in a simple matrix-type liquid crystal device, it is useful to know the degree of alignment irregularity for improvement in alignment steps and finding of inferior products on a production line.

On the other hand, in the above-mentioned optical anisotropy measurement apparatus, the measurement region has a size of several mm in diameter depending on the diameter of the incident beam A. More specifically, the incident laser beam A entering the boundary between the alignment film 208b and the transparent electrode 209b has a beam diameter on the order of 1 mm and the incident beam A enters the boundary obliquely so that the beam A is incident at the boundary in an oval shape having a short axis of ca. 1 mm and a long axis of several mm. Further, the spherical segment glass 203 and the liquid crystal cell 206 are rotated for measurement, so that the actual measurement region becomes a circle of several mm in diameter. Accordingly, it is impossible to measure the pretilt angle and its distribution at minute regions in one pixel of a liquid crystal device by the above-mentioned optical anisotropy measurement apparatus.

Further, in order to know a local irregularity of pretilt angle, it is necessary to change and determine the measurement position in a liquid crystal device. However, in the above-mentioned conventional optical anisotropy measurement apparatus 200 shown in FIGS. 12 and 13, the liquid crystal cell 206 for measurement is integrally formed with the spherical segment glass 203, so that the measurement can be effected at only one region in the liquid crystal cell.

Further, as the liquid crystal cell 206 for measurement is formed integrally with the spherical segment glass 203, it is impossible to use for measurement an actual liquid crystal cell incorporated in a display panel, etc., or a liquid crystal cell produced through steps very close to those for production of an actual liquid crystal cell (e.g., one produced in an identical structure except for using a substrate having a different refractive index.) as an object to be examined, and it is necessary to use a cell for measurement produced through different steps. Accordingly, a considerable extraneous labor is required for the measurement, and information useful for improvement in actual production step is restricted.

SUMMARY OF THE INVENTION

An object of the present invention is to provide an optical anisotropy measurement apparatus allowing an optical anisotropy measurement under desired conditions by disposing a prescribed incident optical system providing a desired beam incident to an object to be examined between a light source and a spherical segment glass, and also an optical anisotropy measurement method using the apparatus.

Another object of the present invention is to provide an optical anisotropy measurement apparatus capable of preventing a deterioration in measurement accuracy by disposing a prescribed incident optical system between a light source and a spherical segment glass to provide a beam comprising parallel light flux incident to an object to be examined, and also an optical anisotropy measurement method using the apparatus.

Another object of the present invention is to provide an optical anisotropy measurement apparatus allowing an optical anisotropy measurement in a minute region of a substance by disposing a prescribed incident optical system between a light source and a spherical segment glass to provide an incident beam having a smaller beam diameter entering an object to be examined, and an optical anisotropy measurement method using the apparatus.

A further object of the present invention is to provide an optical anisotropy measurement apparatus capable of moving an object to be examined on a spherical segment glass so as to allow an optical anisotropy measurement in a desired region of a substance, and also an optical anisotropy measurement method using the apparatus.

A further object of the present invention is to provide an optical anisotropy measurement apparatus allowing an optical anisotropy measurement of a liquid crystal as an object to be examined and allowing the determination of a pretilt angle of the liquid crystal, and an optical anisotropy measurement method using the apparatus.

A still further object of the present invention is to provide a process for producing a liquid crystal device, wherein the above-mentioned apparatus and method are used to measure the optical anisotropy of a liquid crystal in a liquid crystal device and determine a pretilt angle of the liquid crystal, thereby effectively performing improvements in steps for producing a liquid crystal device including an alignment step and finding of inferior products on a production line.

According to the present invention, there is provided an optical anisotropy measurement apparatus, comprising:

a transparent member having a curved surface and a flat surface for mounting an object to be examined thereon, a light source disposed opposite to a first region of the curved surface of the transparent member so as to emit a beam incident through the first region and the transparent member to an outer surface of the object to be examined, a polarizer disposed on the emission side of the light source, an incident optical system disposed between the light source and the first region of the curved surface of the transparent member, a photodetector disposed opposite to a second region of the curved surface of the transparent member so as to detect a beam emitted from the light source, totally reflected at a proximity of the outer surface of the object to be examined and incident thereto through the second region, and an analyzer disposed between the photodetector and the second region of the curved surface of the transparent member.

In a preferred embodiment, the object to be examined is disposed on the flat surface via a liquid having a refractive index substantially equal to that of the transparent member so as to be slidably movable relative to the flat surface of the transparent member.

In another preferred embodiment, the object or substance to be examined is sandwiched between a pair of substrates to form a cell structure, and the cell is disposed on the flat surface via a liquid having a refractive index substantially equal to that of the transparent member so as to be slidably movable relative to the flat surface of the transparent member.

According to another aspect of the present invention, there is provided a method for measuring an optical anisotropy of an object to be examined by using the above-mentioned apparatus.

According to still another aspect of the present invention, there is provided a process for producing a liquid crystal device, including a step of measuring an optical anisotropy of a liquid crystal by the above-mentioned optical anisotropy measurement method.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
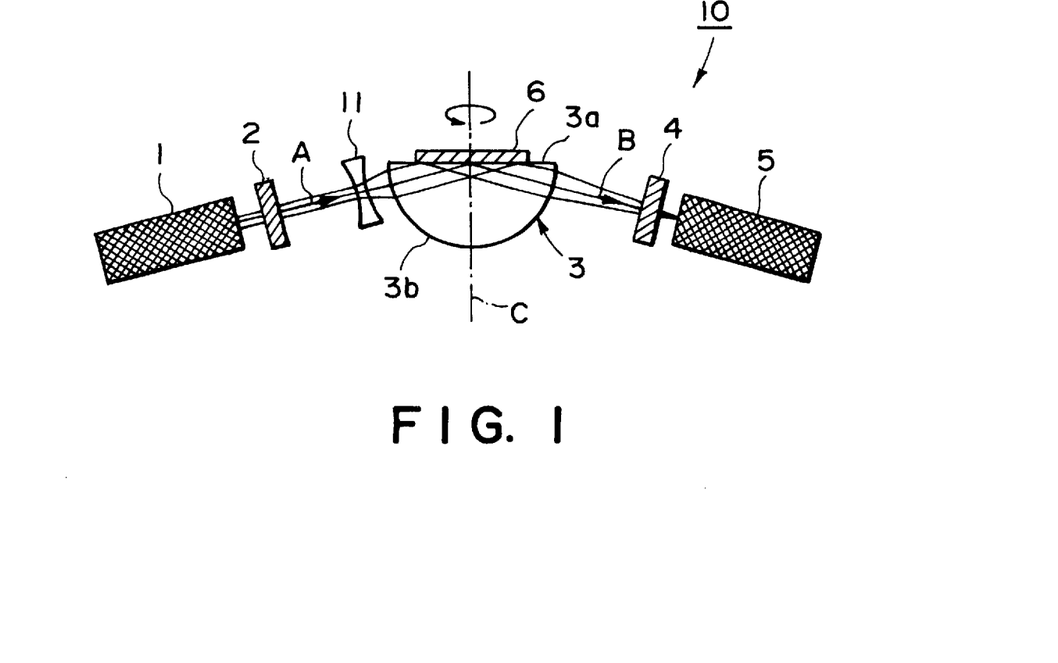
FIGS. 1 to 9 are schematic illustrations of first to ninth embodiments, respectively, of the optical anisotropy measurement apparatus according to the invention.

FIG. 1 is a schematic illustration of a first embodiment of the optical anisotropy measurement apparatus according to the present invention. Referring to FIG. 1, an optical anisotropy measurement apparatus 10 includes a He—Ne laser (light source) 1, a polarizer 2, a spherical segment glass 3 of a hemispherical shape, an analyzer 4 and a photodetector 5, and a liquid crystal cell 6 is formed on a flat surface 3a of the spherical segment glass 3 integrally with the spherical segment glass 3. These members are constituted similarly as the corresponding members in the conventional optical anisotropy measurement apparatus described with reference to FIGS. 12 and 13, and a detailed description thereof is omitted. The optical anisotropy measurement apparatus includes a concave lens 11 (as an incident optical system having a negative power) between the polarizer 2 and the spherical segment glass 3, so that an incident beam A (parallel light flux) emitted from the He—Ne laser 1 is diverged by the concave lens 11. The concave lens 11 and the spherical segment lens 3 are arranged to constitute an afocal optical system, so that the incident beam A is once diverged by the power of the concave lens 11 and then converged by the power of the spherical segment glass 3 to provide a parallel beam (parallel light flux) incident to the liquid crystal cell 6. Herein, the afocal optical system means an optical system such that parallel light flux incident to and transmitted through the optical system will make transmitted parallel light flux provided that reflected light is not considered.

The spherical segment glass 3 may preferably have a shape of a hemisphere or a shape close thereto, and a curvature center in the measurement region or a region close thereto. The spherical segment glass 3 may preferably comprise a high refractive index glass having a refractive index of at least 1.7, more preferably at least 1.75, of, e.g., heavy flint glass. It is possible to alternatively use a transparent material free from optical anisotropy other than glass. It is preferred to use a material having a refractive index larger than that of a liquid crystal layer 207 as an object to be examined.

The light source 1 can be an Ar laser, a semiconductor laser or a beam emission apparatus other than a laser, such as a thermal radiation source, in addition to the He—Ne laser but may preferably comprise an apparatus emitting a beam or light flux that can be condensed. The light source 1 may preferably be one free from aberration such as astigmatism and capable of emitting monochromatic light free from chromatic aberration. The photodetector 5 may comprise an optical power meter, a photomultiplier, etc., but may preferably be one of a high sensitivity.

Now, an optical anisotropy measurement method (method of determining a pretilt angle) by using the optical anisotropy measurement apparatus 10 will be described.

Incident beam A (parallel light flux) emitted from the He—Ne laser 1 is converted into linearly polarized light by passing through the polarizer 2 and becomes a diverged beam by passing through the concave lens 11 to be incident to the spherical segment glass 3 through the spherical surface 3b thereof. The incident beam A (diverged light flux) having entered the spherical segment glass 3 is transformed into a parallel beam (light flux) by the power of the spherical segment glass 3 to be totally reflected at the boundary between an alignment film and a transparent electrode in the liquid crystal cell 6. An evanescent wave occurring during the total reflection penetrates into the liquid crystal layer to interact with liquid crystal molecules, returns into the spherical segment glass 3 and forms an outgoing beam B together with the totally reflected light. The outgoing beam B forms a convergent beam, is emitted from a spherical surface 3b of the spherical segment glass 3, passes through the analyzer 4 and enters the photodetector 5.

When the spherical segment glass 3 is rotated about a rotation axis C, the director of liquid crystal molecules (which is a unit vector representing the orientation of liquid crystal molecules) in the liquid crystal cell 6 is changed relative to the electric field vector of the laser beam A incident to the spherical segment glass 3. Accordingly, corresponding to the rotation angle of the spherical segment glass 3 (i.e., that of the liquid crystal cell 6), the polarization state of the outgoing beam B emitted from the spherical segment glass 3 is changed. By plotting the outputs of the photodetector 5 versus the rotation angle of the spherical segment glass 3 (=the rotation angle of the liquid crystal cell 6), a characteristic curve as shown in FIG. 14 is obtained, and a pretilt angle can be determined from the characteristic curve.

More specifically, the pretilt angle determination may be performed roughly in the following manner. If a maximum intensity near a rotation angle 45 deg. (leftmost peak in FIG. 14) is represented by its peak 1 and a minimum intensity near a rotation angle 90 deg. (valley) is represented by its height (altitude) m, a ratio m/l gives a measure of pretilt angle such that a larger m/l ratio represents a larger pretilt angle and vice versa. For example, a ratio m/l of 0.5 roughly represents a pretilt angle of ca. 10 deg. and a ratio m/l of 0 represents a pretilt angle of ca. 0 deg. while it is affected by $n_o$ and $n_e$ (refractive indices for ordinary and extraordinary rays, respectively) of a liquid crystal concerned.

According to this embodiment shown in FIG. 1, the incident beam B enters the liquid crystal cell 6 in the form of parallel light flux so that the incident angle to the boundary of the alignment film and the transparent electrode is free from spreading so that the deterioration of measurement accuracy can be prevented.

Now, a second embodiment of the optical anisotropy measurement apparatus according to the present invention will be described with reference to FIG. 2, wherein members identical to those in FIG. 1 are denoted by identical reference numerals and the description thereof may be omitted.

Figure 2:
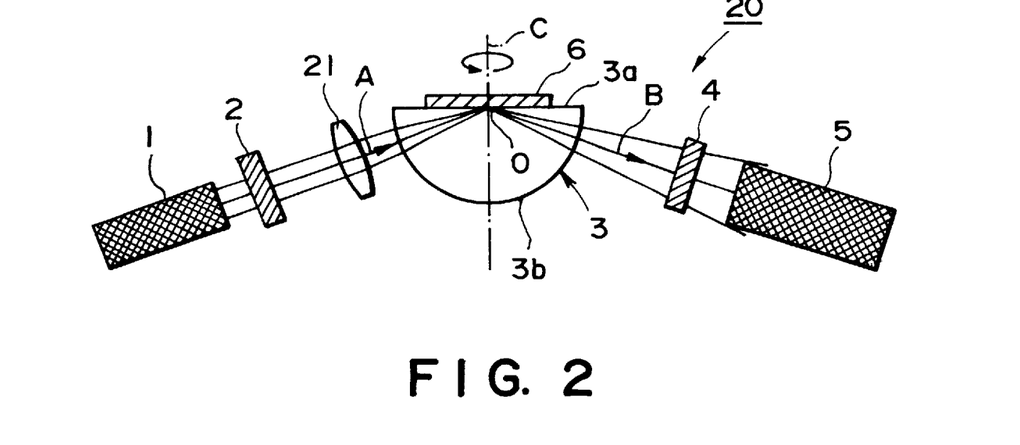

Referring to FIG. 2, an optical anisotropy measurement apparatus 20 includes a convex lens 21 (i.e., an optical system having a positive power).

Incident beam A (parallel light flux) emitted from the He—Ne laser 1 is converged by the convex lens 21 to enter the spherical segment glass 3 and further converged by the spherical segment glass 3 to be converged at a point O of intersection of the rotation axis C and the boundary between the alignment film and the transparent electrode (hereinafter simply called a "convergent point"). The converged incident beam A is totally reflected at the convergent point O. An evanescent wave occurring in the total reflection interacts with liquid crystal molecules, returns into the spherical segment glass 3 and forms an outgoing beam B together with the totally reflected light. The outgoing beam B becomes a divergent beam and is emitted from the spherical segment glass to pass through the analyzer 4 and enter the photodetector 5.

According to this embodiment, the beam diameter of the incident beam A is reduced by the input optical system 21, so that it becomes possible to measure the optical anisotropy of a liquid crystal at a minute region and determine a pretilt angle therefrom. In this embodiment, the input optical system 21 may be arranged so as to reduce a beam diameter of ca. 1 mm of the incident beam A (parallel light flux) emitted from the He—Ne laser to a beam diameter of ca. 10 $\mu$m at the convergent point.

Incidentally, the beam diameter at the convergent point O, i.e., beam diameter on the measurement surface, is principally determined by the N.A. (numerical aperture) of the input optical system 21. Accordingly, if the N.A. of the input optical system 21 is enlarged, it becomes possible to further reduce the size of the measurement region. If the input optical system 21 is completely free from aberration, it is possible to converge the beam down to the diffraction limit. On the other hand, when such an input optical system is used, the incident beam A becomes convergent light flux so that the incident angle to the measurement region is accompanied with a spreading, thus being liable to result in a deterioration in measurement accuracy. However, convergent light flux is approximate to parallel light flux in proximity to the convergent point of the convergent light flux, the spreading of the incident angle is not so serious as to deteriorate the measurement accuracy.

A third embodiment of the optical anisotropy measurement apparatus according to the present invention will now be described with reference to FIG. 3, wherein members identical to those in FIG. 2 are denoted by identical reference numerals and the description thereof may be omitted.

Figure 3:
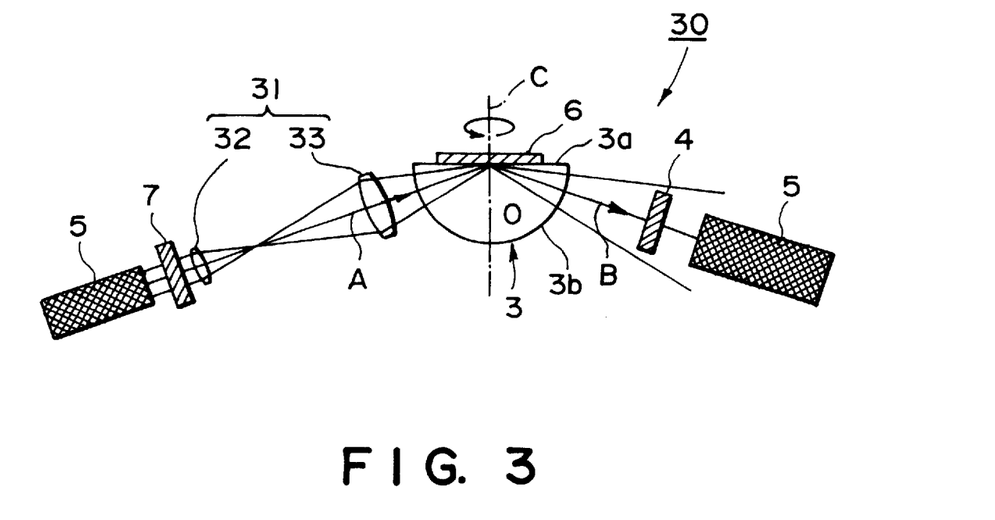

Referring to FIG. 3, an optical anisotropy measurement apparatus 20 includes an input optical system 31 comprising two convex lenses 32 and 33 between the polarizer 2 and the spherical segment glass 3.

In the input optical system 31, the concave lens 32 disposed closer to the polarizer 2 is designed to once converge the incident beam A (parallel light flux) and then convert it into a divergent beam, and the other concave lens 33 is designed to convert the divergent beam into a convergent beam.

In this embodiment, an incident optical system comprising two convex lenses is used to obtain a large N.A. and provide a convergent beam having a reduced beam diameter of 3–5 $\mu$m at the convergent point. Further, the incident optical system 31 is designed to provide a convergent having passed through the optical system 31 and incident to the spherical segment glass 3 with a wave surface having a curvature radius equal to that of the spherical segment glass 3, so that the incident beam A is converged at the convergent point without being refracted at the incidence to the spherical segment glass 3.

FIG. 3 shows an apparatus including an incident optical system comprising two convex lenses but the incident optical system can comprise three or more lenses not only of convex lenses.

According to this embodiment, the beam diameter of the incident beam A can be further reduced by the incident optical system 31, so that it is possible to measure the optical anisotropy of a liquid crystal at a minute region and determine a pretilt angle thereof. More specifically, because of a remarkably improved resolving power, it is possible to detect a fluctuation in pretilt angle, e.g., in one pixel, thereby obtaining data effective for improving the steps for producing a liquid crystal device and the performances of the liquid crystal device per se.

In the above-mentioned second and third embodiments, the incident optical system is disposed so that the incident beam is converged at the boundary between an alignment film and a transparent electrode in the liquid crystal cell 6, but this is not necessary. For example, it is possible to dispose the incident optical system movably in an optical axis direction so that the convergent point can be shifted. It is also possible to dispose a single or plural circular apertures of different sizes between the incident optical system and the spherical segment glass so as to cause a change in effective N.A., whereby the size of measurement region can be changed and it becomes possible to obtain information, e.g., one as to from what size of region, the irregularity in pretilt angle becomes pronounced.

A fourth embodiment of the optical anisotropy measurement apparatus according to the present invention will now be described with reference to FIG. 4, wherein members identical to those in FIG. 3 are denoted by identical reference numerals and the description thereof may be omitted.

Figure 4:
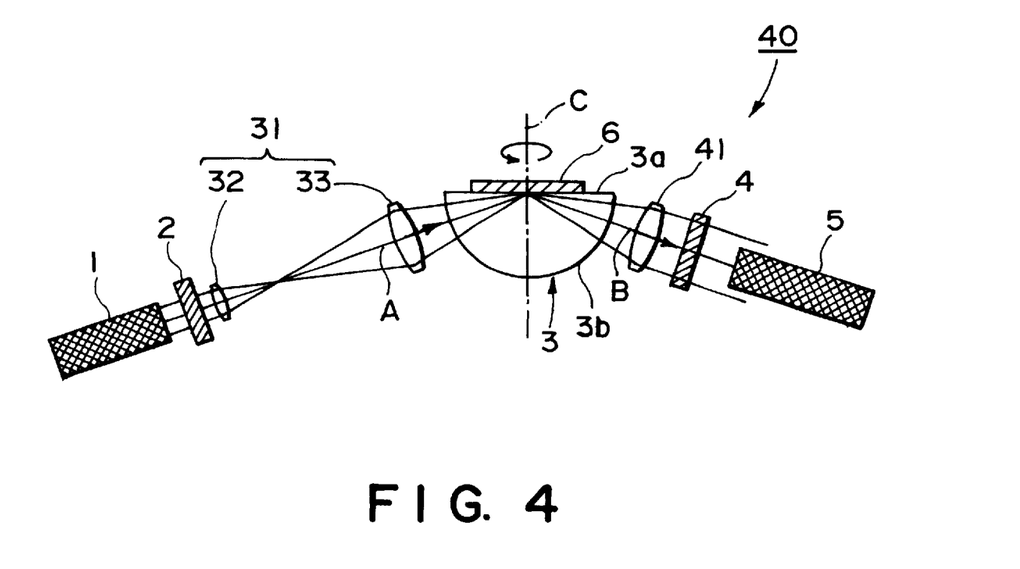

Referring to FIG. 4, an optical anisotropy measurement apparatus 40 has a structure similar to that of the above-described optical anisotropy measurement apparatus 30 shown in FIG. 3 but is different from the latter in that it further includes a first outgoing optical system 41 comprising a convex lens, which is arranged to convert the outgoing beam B emitted from the spherical segment glass 3 in the form of divergent light flux into parallel light flux.

An analyzer 4 composed of a polarizing element such as a Glan-Thompson prism, generally has an incident angle-dependence. More specifically, when a beam entering the analyzer 4 comprises various angle components, including those providing an incident angle to the analyzer exceeding a tolerable range (ca. ±7 degrees in the case of a Glan-Thomson prim), the performance of the analyzer 4 is deteriorated, e.g., so as to allow the transmission of a polarization component having a polarization perpendicular to that of the analyzer 4, thus resulting in an inferior measurement accuracy. According to this embodiment, however, the beam entering the analyzer 4 has been transformed into parallel light flux by the outgoing optical system 41, so that such an inferior measurement accuracy bean be obviated.

The first outgoing optical system 41 need not necessarily be composed of a single convex lens but may comprise plural lenses.

A fifth embodiment of the optical anisotropy measurement apparatus according to the present invention will now be described with reference to FIG. 5, wherein members identical to those in FIG. 4 are denoted by identical reference numerals and the description thereof may be omitted.

Figure 5:
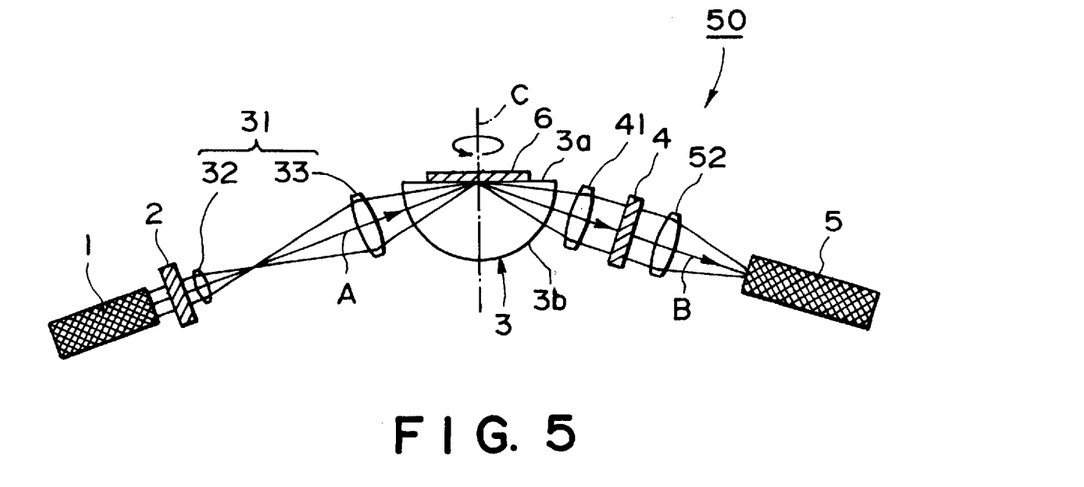

Referring to FIG. 5, an optical anisotropy measurement apparatus 50 has a structure similar to that of the above-described optical anisotropy measurement apparatus 40 shown in FIG. 4 but is different from the latter in that it further includes a second outgoing optical system 52 comprising a convex lens, which is arranged to convert the parallel light flux outgoing from the analyzer 4 into convergent light flux, thereby reducing the beam diameter of the beam reaching the photodetector 5.

According to this embodiment, the parallel light flux (beam) is converged by the second outgoing optical system 52 before entering the photodetector 5, so that the light quantity entering the photodetector 5 is increased to provide an improved detecting efficiency.

The second outgoing optical system 52 need not necessarily be composed of a single convex lens but may comprise plural lenses.

A sixth embodiment of the optical anisotropy measurement apparatus according to the present invention will now be described with reference to FIG. 6, wherein members identical to those in FIG. 5 are denoted by identical reference numerals and the description thereof may be omitted.

Figure 6:
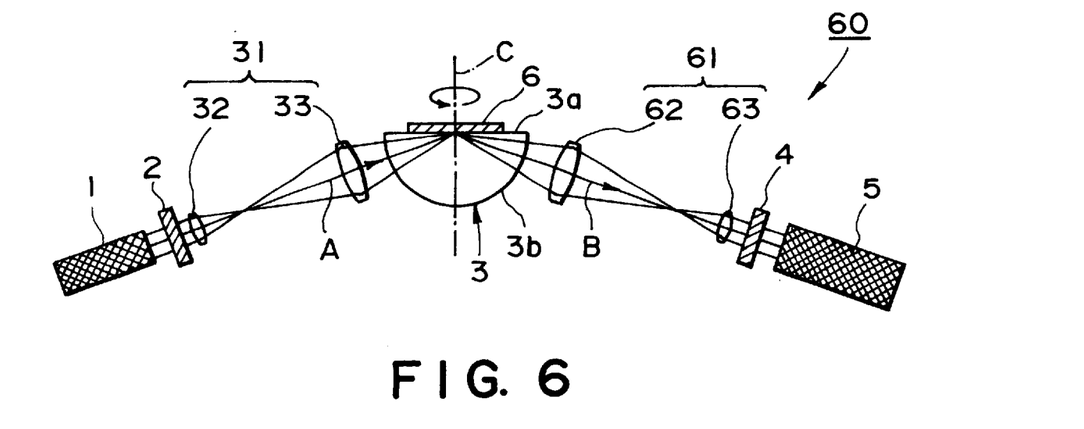

Referring to FIG. 6, an optical anisotropy measurement apparatus 60 has a structure similar to that of the above-described optical anisotropy measurement apparatus 50 shown in FIG. 5 but is different from the latter in that it includes a third outgoing optical system 61 comprising two convex lens 62 and 63 disposed between the spherical segment glass 3 and the analyzer 4. The third outgoing optical system 61 is arranged so that the outgoing beam B emitted from the spherical segment lens 3 is converted first into convergent light flux by the first concave lens 62 and then into parallel light flux by the second concave lens 63. Further, in this embodiment, the input optical system 31 and the output optical system 61 are arranged as a pair of transversely symmetrical lens systems.

According to this embodiment, the beam entering the analyzer 4 is composed of parallel light flux so that the deterioration in measurement accuracy can be obviated. Further, the beam diameter of the outgoing beam B is reduced, so that the light quantity entering the photodetector 5 is increased to provide an improved detection efficiency.

The third outgoing optical system 61 need not necessarily be composed of two convex lenses but may comprise three or more lenses.

A seventh embodiment of the optical anisotropy measurement apparatus according to the present invention will now be described with reference to FIG. 7, wherein members identical to those in FIG. 2 are denoted by identical reference numerals and the description thereof may be omitted.

Figure 7:
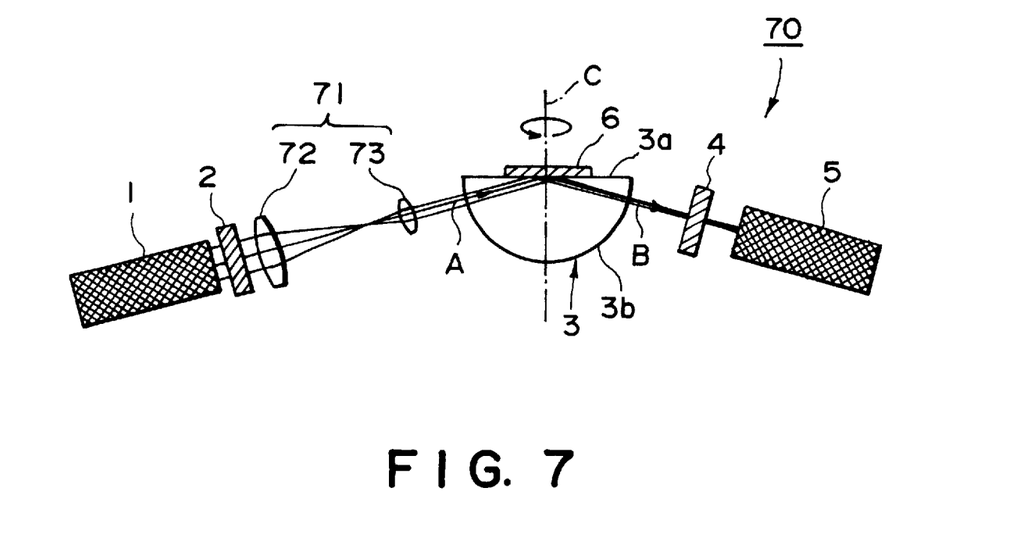

Referring to FIG. 7, an optical anisotropy measurement apparatus 70 includes a beam expander (input optical system) 71 comprising two lenses 72 and 73 disposed between the polarizer 2 and the spherical segment glass 3, so that the incident beam A (parallel light flux) is reduced in beam diameter while retaining the parallel flux state.

According to this embodiment, the incident beam A in the form of linearly polarized light having passed through a polarizer 2 is reduced in beam diameter by the beam expander 71 and incident to the spherical segment glass 3 in a parallel flux state, thereby allowing a measurement of a region on the order of several tens μm in diameter by using substantially parallel light.

In this embodiment, the beam expander 71 is composed of two convex lenses, but this is not limitative.

It is also possible to use an incident beam to a measurement region in the form of completely parallel flux, e.g., by disposing a concave lens between the beam expander 71 and the spherical segment glass 3.

Figure 8:
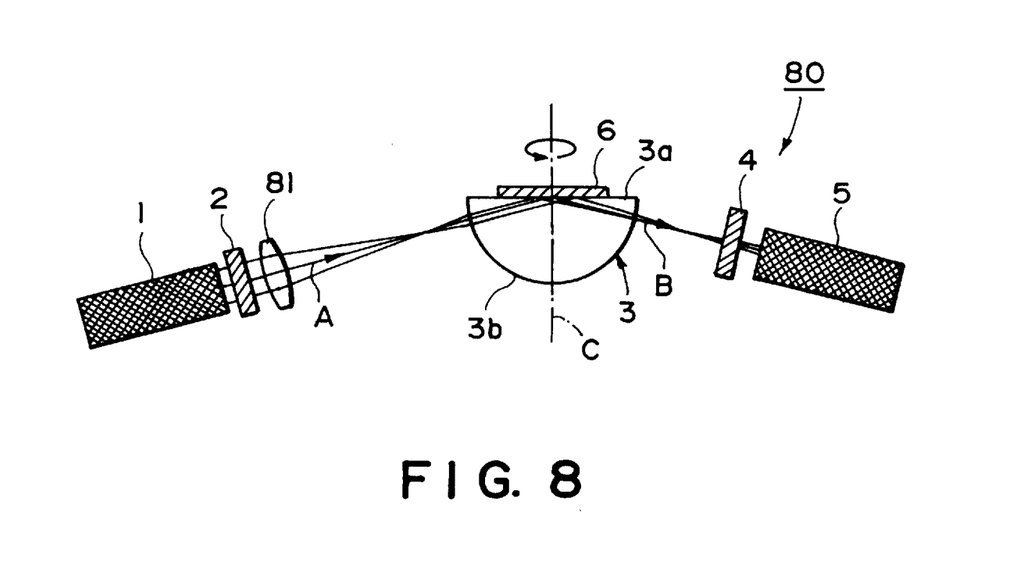

FIG. 8 shows an eighth embodiment of the optical anisotropy measurement apparatus according to the present invention, whereby the incident beam A is reduced in beam diameter and is caused to be incident to the measurement region in the form of completely parallel light flux. In FIG. 8, members identical to those in FIG. 2 are denoted by identical reference numerals and the description thereof may be omitted.

Referring to FIG. 8, an optical anisotropy measurement apparatus 80 includes an incident optical system 81 comprising a convex lens disposed between the polarizer 2 and the spherical segment glass 3 so as to reduce the beam diameter of an incident beam A (parallel light flux) having passed through the polarizer 2. Further, the incident optical system 81 and the spherical segment glass 3 are designed to constitute an afocal optical system, whereby the incident beam is reduced in beam diameter and incident to the measurement region while retaining a parallel light flux state. In this instance, when a convex lens having a focal length of 100–200 mm is used to constitute the incident optical system 81, the incident beam A entering the measurement region may have a reduced beam diameter on the order of several tens μm.

A ninth embodiment of the optical anisotropy measurement apparatus according to the present invention will now be described with reference to FIGS. 9 and 10, wherein members identical to those in FIG. 2 are denoted by identical reference numerals and the description thereof may be omitted.

Referring to these figures, an optical anisotropy measurement apparatus 90 is designed to mount a liquid crystal cell 92 movably or slidably on a flat surface 3a of a spherical segment glass 3.

The flat surface 3a of the spherical segment glass 3 is coated with a refractive index-matching liquid 91 (of, e.g., methylene iodide-based liquid or arsenic tribromide/ disulfide-based liquid) and the liquid crystal cell 92 is mounted on the flat surface 3a via the refractive index-matching liquid 91. The refractive index-matching liquid 91 is dammed up by a peripheral rim 3C, which can however be omitted depending on the quantity and/or the viscosity of the liquid.

An incident beam A emitted from a He—Ne laser 1 passes through the polarizer 2, enters the spherical segment glass 3 through its spherical surface 3b and is totally reflected within the liquid crystal cell 92 to form an outgoing beam B. The beam B is emitted through the spherical surface of the spherical segment 3 to pass through an analyzer 4 and enters a photodetector 5.

Figure 10:
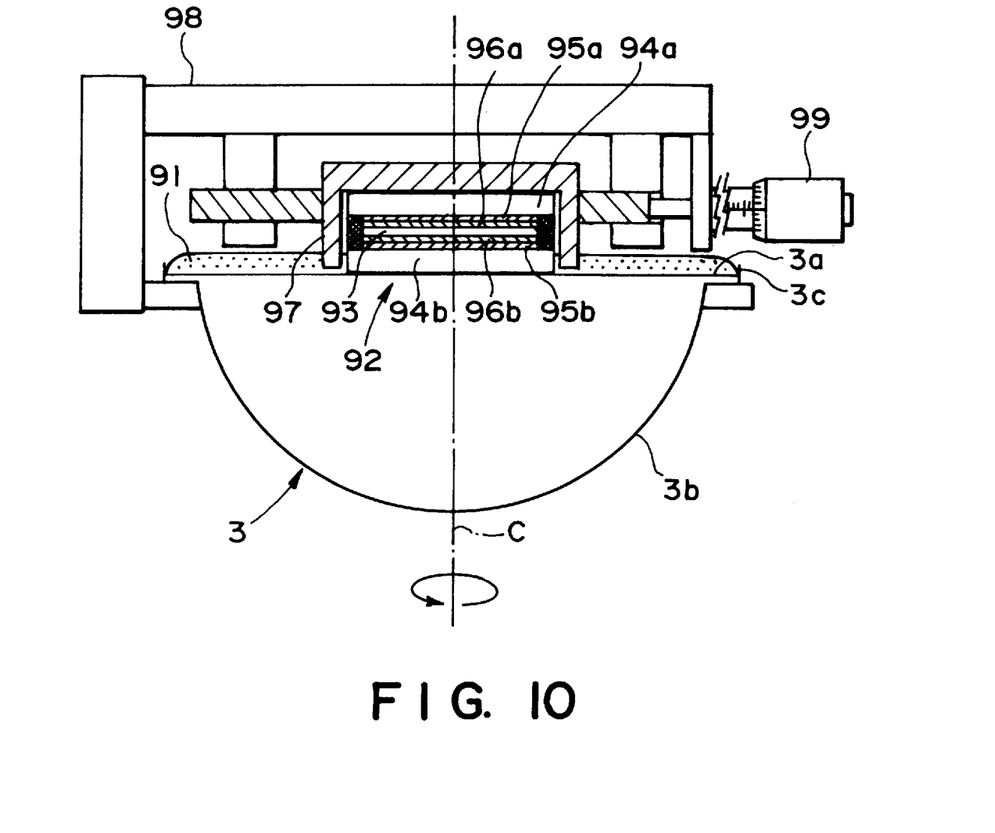
FIG. 10 is an enlarged illustration of a part of the ninth embodiment of the optical anisotropy measurement apparatus.

As shown in FIG. 10, the liquid crystal cell 92 comprises a pair of glass substrates 94a and 94b having thereon transparent electrodes 95a, 95b of, e.g., ca. 0.1 μm-thick ITO films having a refractive index of ca. 1.95, and alignment films 96a, 96b of, e.g., ca. 0.05 μm-thick polyimide films having a refractive index of ca. 1.6, respectively, and a liquid crystal 93 injected between the alignment films 96a and 96b. The liquid crystal cell 92 is held within a liquid crystal cell holder 97 and on the flat surface 3a of the spherical segment glass 3 so that the lower glass substrate 94b thereof is dipped within the refractive index-matching liquid 91.

The liquid crystal cell holder 97 is supported movably by a spherical segment glass holder 98 also holding the spherical segment glass 3 and driven at a high accuracy by a drive mechanism (not shown). For example, the spherical segment glass 3 may be fixed, and the liquid crystal cell 92 may be moved or slided along the flat surface 3a of the spherical segment glass 3.

The spherical segment glass holder 98 is equipped with a micrometer 99, by which the measurement position of the liquid crystal cell 92 can be accurately confirmed. Such micrometer may be provided in a plurality, e.g., so as to have axes crossing each other at right angles, thereby allowing a two-dimensional position confirmation of the liquid crystal cell 92.

Further, the spherical segment glass holder 98 is provided with a rotation apparatus (not shown) for rotating the spherical segment glass 3 about its central axis (rotation axis) C, so that the spherical segment glass 3 and the liquid crystal cell 92 are integrally rotated about the rotation axis C.

The spherical segment glass 3 may be composed of a glass material having a refractive index almost identical to that of the glass substrate 94b of the liquid crystal cell 92, and the refractive index-matching liquid may also comprise a liquid (e.g., methylene iodide-based liquid, etc. as described above) having a refractive index almost identical to that of the glass substrate 94b. Herein, almost identical refractive indexes mean such a closeness of refractive index as to avoid a total reflection of the incident beam A at the boundary between the spherical segment glass 3 and the matching liquid 91, and at the boundary between the matching liquid 91 and the liquid crystal cell 92, and may be determined depending on the incident angle. More specifically, the refractive index difference between the spherical segment glass 3 and the matching liquid 91 and the refractive index difference between the matching liquid 91 and the glass substrate 94 may preferably be within a range of ±0.05, respectively.

The spherical segment glass 3 and the glass substrate 94b may preferably comprise a high-refractive index glass, such as heavy flint glass, having a refractive index of at least 1.7, more preferably at least 1.75. It is also possible to use a transparent material free from optical anisotropy instead of glass. In this instance, a material having a larger refractive index than the liquid crystal layer 93 is suitably used. The glass substrate 94a can also be composed of a high refractive index glass.

In this embodiment, the flat surface 3a of the spherical segment glass 3 has a larger area than the liquid crystal cell but can have a smaller area than the latter.

The optical anisotropy (and pretilt angle) of the liquid crystal layer 93 may be measured by using the above-mentioned optical anisotropy measurement apparatus 90 as follows.

The incident beam A emitted from the He—Ne laser passes through the polarizer 2 to be linearly polarized light and enters the spherical segment glass 3 through the spherical surface 3b. The incident beam A having entered the spherical segment glass 3 passes through the flat surface 3a of the spherical segment glass 3 and the refractive index-matching liquid 91 to enter the liquid crystal cell 92.

As the spherical segment glass 3 has a refractive index almost identical to the glass substrate 94b of the liquid crystal cell 92, and the refractive index-matching liquid 91 also has a refractive index almost identical to those of the glass substrate 94b and the spherical segment glass 3, the incident beam A having entered the spherical segment glass is caused to enter the glass substrate 94b without causing refraction.

The incident beam A having entered the glass substrate 94b is totally reflected at the boundary between the transparent electrode 95b and the alignment film 96b. During the total reflection, an evanescent wave occurs, penetrates into the liquid crystal layer 93 to interact with liquid crystal molecules and returns to the spherical segment glass 3 to form an outgoing beam B together with the totally reflected light. The outgoing between B emitted from the spherical surface 3b of the spherical segment 3 is once conveyed to pass through the analyzer 4 having a polarization direction perpendicular to that of the polarizer 2, whereby only a light component having a polarization direction perpendicular to the incident beam A reaches the photodetector 5.

Now, the spherical segment glass 3 is rotated about the rotation axis C similarly as in the first embodiment, and the outputs from the photodetector 5 are plotted versus the rotation angle of the spherical segment glass 3 (=the rotation angle of the liquid crystal cell 92), whereby a characteristic curve as shown in FIG. 14 is obtained, and a pretilt angle can be determined from the characteristic curve.

In this embodiment, as the liquid crystal cell 92 is mounted on the flat surface 3a of the spherical segment glass 3 in a state that the glass substrate 94b thereof is dipped in the refractive index-matching liquid 1, an actual liquid crystal cell incorporated in a display panel, etc., or a liquid crystal cell produced through steps very close to those for production of an actual liquid crystal cell (e.g., one produced in an identical structure except for using a high-refractive index glass sheet for the substrate) can be used as an object to be examined for the measurement of optical anisotropy of a liquid crystal to determine its pretilt angle. Further, it is also possible to cut a portion of a liquid crystal device to form a liquid crystal cell for measurement.

Further, in this embodiment, the liquid crystal cell 92 is held in the liquid crystal cell holder 97, which can be moved by a drive mechanism (not shown) to move the liquid crystal cell 92 along the flat surface 3a of the spherical segment glass 3 while accurately measuring the moving distance of the liquid crystal cell holder 97 to confirm the measurement position of the liquid crystal cell 92, whereby it is possible to measure a pretilt angle at a desired position of the liquid crystal layer 93.

According to this embodiment, as the pretilt angle of an actual liquid crystal cell or a liquid crystal prepared through steps close to those for production of an actual liquid crystal cell can be measured at desired position, it is possible to obtain information very important for improving the steps for production of a liquid crystal device or the performance of a liquid crystal device per se. Further, by incorporating the optical anisotropy measurement apparatus according to this embodiment in an actual production line for a liquid crystal devices to produce a liquid crystal device, it becomes possible to produce high-quality liquid crystal devices without producing an unsatisfactory product.

The optical anisotropy measurement apparatus 90 according to this embodiment can be combined with various optical systems used in the first to eighth embodiments to obtain effects similar to those in such embodiments.

Figure 9:
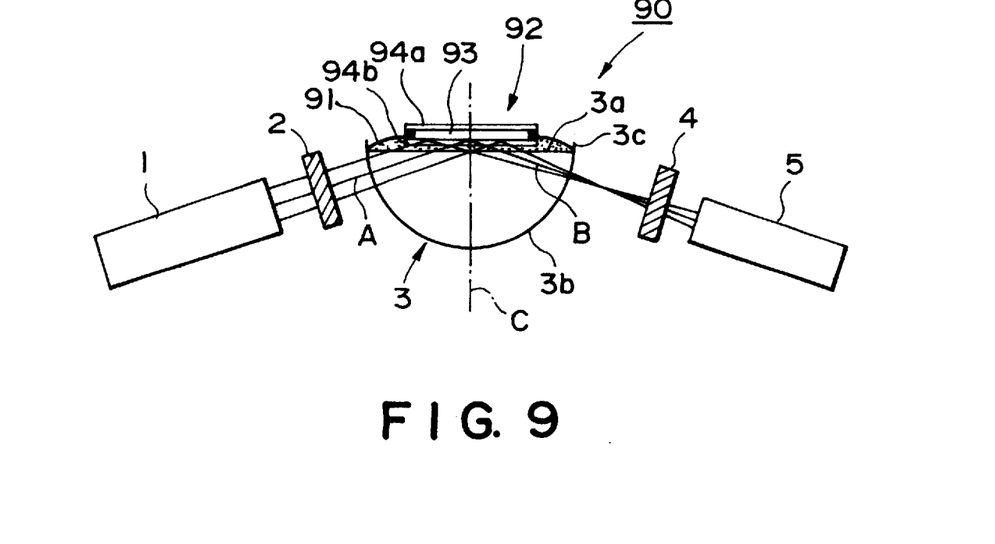

As an example of such a combination, a tenth embodiment of the optical anisotropy measurement apparatus according to the present invention will be described with reference to FIG. 11, wherein members identical to those in FIG. 9 are denoted by identical reference numerals and the description thereof may be omitted.

Figure 11:
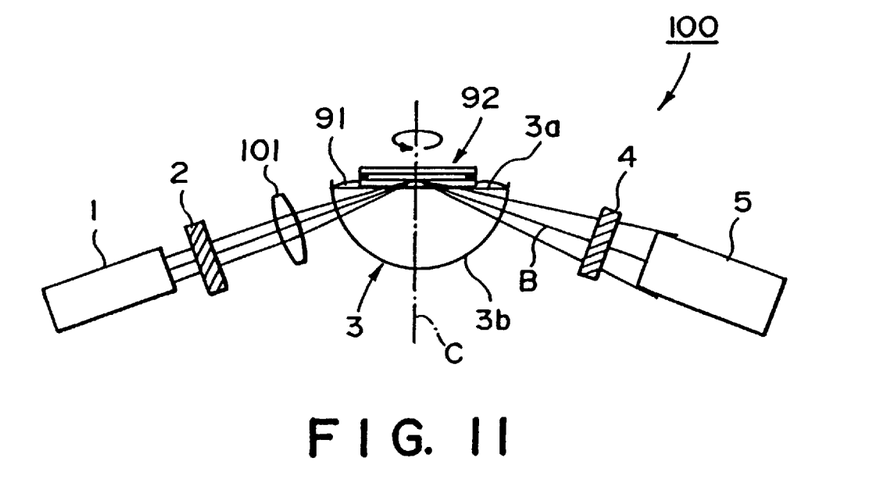
FIG. 11 is a schematic illustration of a tenth embodiment of the optical anisotropy measurement apparatus according to the invention.

Referring to FIG. 11, an optical anisotropy measurement apparatus 100 includes a convex lens 101 (incident optical system) between the polarizer 2 and the spherical segment glass 3. The other structures are similar to those in the optical anisotropy measurement apparatus 90 in the ninth embodiment.

According to this embodiment, the size of the measurement region for measurement of a pretilt angle in a liquid crystal layer can be reduced to several $\mu$m to several tens $\mu$m by converging the incident beam A in proximity to the measurement region, so that a pretilt angle of a liquid crystal layer in a desired position in one pixel can be measure to evaluate the irregularity in pretilt angle in a pixel.

According to this embodiment, as the pretilt angle of an actual liquid crystal cell or a liquid crystal prepared through steps close to those for production of an actual liquid crystal cell can be measured in a small region at desired position, it is possible to obtain information very important for improving the steps for production of a liquid crystal device or the performance of a liquid crystal device per se. Further, by incorporating the optical anisotropy measurement apparatus according to this embodiment in an actual production line for a liquid crystal devices to produce a liquid crystal device, it becomes possible to produce high-quality liquid crystal devices without producing an unsatisfactory product.

What is claimed is:

1. An optical anisotropy measurement apparatus comprising:

a transparent member having a curved surface and a flat surface for movably mounting an object to be examined thereon, said object to be examined being a liquid crystal device comprising a pair of transparent substrates and a liquid crystal disposed therebetween, a light source disposed opposite to a first region of the curved surface of the transparent member so as to emit a beam incident through the first region and the transparent member to an outer surface of the object to be examined, a polarizer disposed on the emission side of the light source, an incident optical system disposed between the light source and the first region of the curved surface of the transparent member, so as to provide a reduced diameter of the beam incident to the outer surface of the object to be examined, a photodetector disposed opposite to a second region of the curved surface of the transparent member so as to detect a beam emitted from the light source, totally reflected at a proximity of the outer surface of the object to be examined and incident thereto through the second region, an analyzer disposed between the photodetector and the second region of the curved surface of the transparent member, means for moving the object to be examined in a direction parallel to the flat surface of the transparent member, and means for monitoring a local position under examination of the object to be examined.

2. An apparatus according to claim 1, wherein said object to be examined is disposed in a container which is mounted movably relative to the flat surface.

3. An apparatus according to claim 1, wherein said transparent member is a spherical segment member of hemispherical shape.

4. An apparatus according to claim 1, wherein said incident optical system has a negative power.

5. An apparatus according to claim 1, wherein said incident optical system and said transparent member form an afocal optical system.

6. An apparatus according to claim 1, wherein said incident optical system has a positive power.

7. An apparatus according to claim 1, wherein said beam emitted from the light source is caused to have a reduced beam diameter by said input optical system.

8. An apparatus according to claim 7, wherein said input optical system is an afocal optical system.

9. An apparatus according to claim 1, wherein said input optical system has a focal point which coincides with a curvature center of said transparent member in proximity to the outer surface of said object to be examined.

10. An apparatus according to claim 3, further including a first outgoing optical system having a positive power disposed between said spherical segment member and said analyzer.

11. An apparatus according to claim 10, wherein said first outgoing optical system has a focal point which coincides with a curvature center of the spherical segment member in proximity to the outer surface of said object to be examined.

12. An apparatus according to claim 1, further including a second outgoing optical system between said transparent member and said analyzer.

13. An apparatus according to claim 1, wherein said transparent member has a refractive index larger than that of said object to be examined.

14. An apparatus according to claim 1, wherein said input optical system is disposed movably in its optical axis direction.

15. An apparatus according to claim 1, wherein said beam emitted from said light source has a wave surface having a curvature center coinciding with that of the curved surface of the transparent member at the curved surface of the transparent member.

16. An apparatus according to claim 1, wherein said object to be examined is a liquid crystal.

17. An apparatus according to claim 1, wherein said transparent member comprises glass.

18. An apparatus according to claim 1, wherein said transparent member has a refractive index of at least 1.7.

19. An optical anisotropy measurement apparatus comprising:
- a transparent member having a curved surface and a flat surface for mounting an object to be examined thereon, said object to be examined being a liquid crystal device comprising a pair of transparent substrates and a liquid crystal disposed therebetween,
- a liquid having a refractive index almost equal to that of the transparent member disposed between the transparent member and the object to be examined so as to support the object to be examined movably relative to the transparent member,
- a light source disposed opposite to a first region of the curved surface of the transparent member so as to emit a beam incident through the first region and the transparent member to an outer surface of the object to be examined,
- a polarizer disposed on the emission side of the light source,
- an incident optical system disposed between the light source and the first region of the curved surface of the transparent member, so as to provide a reduced diameter of the beam incident to the outer surface of the object to be examined,
- a photodetector disposed opposite to a second region of the curved surface of the transparent member so as to detect a beam emitted from the light source, totally reflected at a proximity of the outer surface of the object to be examined and incident thereto through the second region,
- an analyzer disposed between the photodetector and the second region of the curved surface of the transparent member,
- means for moving the object to be examined in a direction parallel to the flat surface of the transparent member, and
- means for monitoring a local position under examination of the object to be examined.

20. An apparatus according to claim 19, wherein said transparent member is a spherical of hemispherical shape segment member.

21. An apparatus according to claim 19, wherein said transparent member and said liquid have a difference in refractive index therebetween within a range of ±0.05.

22. An optical anisotropy measurement apparatus comprising:
- a transparent member having a curved surface and a flat surface for mounting thereon a liquid crystal device comprising a liquid crystal to be examined between a pair of substrates,
- a liquid having a refractive index almost equal to that of the transparent member disposed between the transparent member and the liquid crystal device so as to support the liquid crystal device movably relative to the transparent member,
- a light source disposed opposite to a first region of the curved surface of the transparent member so as to emit a beam incident through the first region and the transparent member to an outer surface of the object to be examined,
- a polarizer disposed on the emission side of the light source,
- a photodetector disposed opposite to a second region of the curved surface of the transparent member so as to detect a beam emitted from the light source, totally reflected at a proximity of the outer surface of the object to be examined and incident thereto through the second region,
- an analyzer disposed between the photodetector and the second region of the curved surface of the transparent member,
- means for moving the liquid crystal device in a direction parallel to the flat surface of the transparent member, and
- means for monitoring a local position under examination of the liquid crystal device.

23. An apparatus according to claim 22, wherein said transparent member is a spherical segment member of hemispherical shape.

24. An apparatus according to claim 22, wherein said transparent member and said liquid have a difference in refractive index therebetween within a range of ±0.05.

25. An apparatus according to claim 22, wherein the substrate of the cell on the transparent member side has a refractive index which has a difference within a range of ±0.05 from that of said liquid.

26. An apparatus according to claim 19 or 22, further comprising an input optical system disposed between the light source and the transparent member.

27. An apparatus according to claim 26, wherein said input optical system has a negative power.

28. An apparatus according to claim 27, wherein said input optical system and said transparent member form an afocal optical system.

29. An apparatus according to claim 26, wherein said input optical system has a positive power.

30. An apparatus according to claim 26, wherein said input optical system has a function of providing a reduced beam diameter to a beam emitted from the light source.

31. An apparatus according to claim 30, wherein said input optical system as a whole constitutes an afocal optical system.

32. An apparatus according to claim 26, wherein said input optical system has a focal point coinciding with a curvature center of the transparent member in proximity to an outer surface of the object to be examined.

33. An apparatus according to claim 26, further comprising a first outgoing optical system having a positive power between the transparent member and the analyzer.

34. An apparatus according to claim 33, wherein said first outgoing optical system has a focal point coinciding with a curvature center of the transparent member.

35. An apparatus according to claim 26, further comprising a second outgoing optical system having a positive power between the analyzer and the photodetector.

36. An apparatus according to claim 26, wherein said transparent member has a refractive index larger than that of the object to be examined.

37. An apparatus according to claim 26, wherein said input optical system is disposed movably in a direction of its optical axis.

38. An apparatus according to claim 26, wherein said incident optical system is disposed to provide the beam emitted from the light source with a wave surface at the spherical surface of the transparent member, said wave surface having a curvature center coinciding with that of the spherical surface.

39. An optical anisotropy measurement method comprising:

providing an optical anisotropy measurement apparatus, comprising:
 a transparent member having a curved surface and a flat surface for movably mounting an object to be examined thereon, said object to be examined being a liquid crystal device comprising a pair of transparent substrates and a liquid crystal disposed therebetween,
 a light source disposed opposite to a first region of the curved surface of the transparent member so as to emit a beam incident through the first region and the transparent member to an outer surface of the object to be examined,
 a polarizer disposed on the emission side of the light source,
 an incident optical system disposed between the light source and the first region of the curved surface of the transparent member, so as to provide a reduced diameter of the beam incident to the outer surface of the object to be examined,
 a photodetector disposed opposite to a second region of the curved surface of the transparent member so as to detect a beam emitted from the light source, totally reflected at a proximity of the outer surface of the object to be examined and incident thereto through the second region,
 an analyzer disposed between the photodetector and the second region of the curved surface of the transparent member,
 means for moving the object to be examined in a direction parallel to the flat surface of the transparent member, and
 means for monitoring a local position under examination of the object to be examined; and
measuring an optical anisotropy of an object to be examined by using an optical anisotropy measurement apparatus provided in said providing step.

40. A process for producing a liquid crystal device comprising:

manufacturing a liquid crystal device;
providing an optical anisotropy measurement apparatus comprising:
 a transparent member having a curved surface and a flat surface for movably mounting an object to be examined thereon, said object to be examined being a liquid crystal device comprising a pair of transparent substrates and a liquid crystal disposed therebetween,
 a light source disposed opposite to a first region of the curved surface of the transparent member so as to emit a beam incident through the first region and the transparent member to an outer surface of the object to be examined,
 a polarizer disposed on the emission side of the light source,
 an incident optical system disposed between the light source and the first region of the curved surface of the transparent member, so as to provide a reduced diameter of the beam incident to the outer surface of the object to be examined,
 a photodetector disposed opposite to a second region of the curved surface of the transparent member so as to detect a beam emitted from the light source, totally reflected at a proximity of the outer surface of the object to be examined and incident thereto through the second region,
 an analyzer disposed between the photodetector and the second region of the curved surface of the transparent member,
 means for moving the object to be examined in a direction parallel to the flat surface of the transparent member, and
 means for monitoring a local position under examination of the object to be examined; and
measuring an optical anisotropy of the liquid crystal manufactured in said manufacturing step using the optical anisotropy measurement apparatus provided in said providing step.

41. An optical anisotropy measurement method comprising:

providing an optical anisotropy measurement apparatus comprising:
 a transparent member having a curved surface and a flat surface for mounting an object to be examined thereon, said object to be examined being a liquid crystal device comprising a pair of transparent substrates and a liquid crystal disposed therebetween,
 a liquid having a refractive index almost equal to that of the transparent member disposed between the transparent member and the object to be examined so as to support the object to be examined movably relative to the transparent member,
 a light source disposed opposite to a first region of the curved surface of the transparent member so as to emit a beam incident through the first region and the transparent member to an outer surface of the object to be examined,
 a polarizer disposed on the emission side of the light source,
 an incident optical system disposed between the light source and the first region of the curved surface of the transparent member, so as to provide a reduced diameter of the beam incident to the outer surface of the object to be examined,
 a photodetector disposed opposite to a second region of the curved surface of the transparent member so as to detect a beam emitted from the light source, totally reflected at a proximity of the outer surface of the object to be examined and incident thereto through the second region,
 an analyzer disposed between the photodetector and the second region of the curved surface of the transparent member,
 means for moving the liquid crystal device in a direction parallel to the flat surface of the transparent member, and
 means for monitoring a local position under examination of the liquid crystal device; and
measuring an optical anisotropy of an object to be examined by using an optical anisotropy measurement apparatus provided in said providing step.

42. An optical anisotropy measurement method comprising:

providing an optical anisotropy measurement apparatus comprising:

a transparent member having a curved surface and a flat surface for mounting thereon a liquid crystal device comprising a liquid crystal to be examined between a pair of substrates, a liquid having a refractive index almost equal to that of the transparent member disposed between the transparent member and the liquid crystal device so as to support the liquid crystal device movably relative to the transparent member, a light source disposed opposite to a first region of the curved surface of the transparent member so as to emit a beam incident through the first region and the transparent member to an outer surface of the object to be examined, a polarizer disposed on the emission side of the light source, a photodetector disposed opposite to a second region of the curved surface of the transparent member so as to detect a beam emitted from the light source, totally reflected at a proximity of the outer surface of the object to be examined and incident thereto through the second region, an analyzer disposed between the photodetector and the second region of the curved surface of the transparent member, means for moving the liquid crystal device in a direction parallel to the flat surface of the transparent member, and means for monitoring a local position under examination of the liquid crystal device; and measuring an optical anisotropy of an object to be examined by using an optical anisotropy measurement apparatus provided in said providing step.

43. A process for producing a liquid crystal device comprising:

manufacturing a liquid crystal device;

providing an optical anisotropy measurement apparatus comprising:

a transparent member having a curved surface and a flat surface for mounting an object to be examined thereon, said object to be examined being a liquid crystal device comprising a pair of transparent substrates and a liquid crystal disposed therebetween, a liquid having a refractive index almost equal to that of the transparent member disposed between the transparent member and the object to be examined so as to support the object to be examined movably relative to the transparent member, a light source disposed opposite to a first region of the curved surface of the transparent member so as to emit a beam incident through the first region and the transparent member to an outer surface of the object to be examined, a polarizer disposed on the emission side of the light source, an incident optical system disposed between the light source and the first region of the curved surface of the transparent member, so as to provide a reduced diameter of the beam incident to the outer surface of the object to be examined, a photodetector disposed opposite to a second region of the curved surface of the transparent member so as to detect a beam emitted from the light source, totally reflected at a proximity of the outer surface of the object to be examined and incident thereto through the second region, an analyzer disposed between the photodetector and the second region of the curved surface of the transparent member, means for moving the object to be examined in a direction parallel to the flat surface of the transparent member, and means for monitoring a local position under examination of the object to be examined; and measuring an optical anisotropy of the liquid crystal device manufactured in said manufacturing step using the optical anisotropy measurement apparatus provided in said providing step.

44. A process for producing a liquid crystal device comprising:

manufacturing a liquid crystal device;

providing an optical anisotropy measurement apparatus comprising:

a transparent member having a curved surface and a flat surface for mounting thereon a liquid crystal device comprising a liquid crystal to be examined between a pair of substrates, a liquid having a refractive index almost equal to that of the transparent member disposed between the transparent member and the liquid crystal device so as to support the liquid crystal device movably relative to the transparent member, a light source disposed opposite to a first region of the curved surface of the transparent member so as to emit a beam incident through the first region and the transparent member to an outer surface of the object to be examined, a polarizer disposed on the emission side of the light source, a photodetector disposed opposite to a second region of the curved surface of the transparent member so as to detect a beam emitted from the light source, totally reflected at a proximity of the outer surface of the object to be examined and incident thereto through the second region, an analyzer disposed between the photodetector and the second region of the curved surface of the transparent member, means for moving the liquid crystal device in a direction parallel to the flat surface of the transparent member, and means for monitoring a local position under examination of the liquid crystal device; and measuring an optical anisotropy of the liquid crystal device manufactured in said manufacturing step using the optical anisotropy measurement apparatus provided in said providing step.

* * * * *

UNITED STATES PATENT AND TRADEMARK OFFICE
CERTIFICATE OF CORRECTION

PATENT NO. : 5,838,453

DATED : November 17, 1998

INVENTOR(S) : Ohsaki et al.

It is certified that error appears in the above-identified patent and that said Letters Patent is hereby corrected as shown below:

COLUMN 4:

Line 14, "index.)" should read --index)--.

COLUMN 13:

Line 25, "a" should be deleted; and
Line 62, "a" (first occurrence) should be deleted.

COLUMN 15:

Line 54, "of hemispherical shape" should be deleted; and
Line 55, "member." should read --member of hemispherical shape.--.

Signed and Sealed this

Twentieth Day of July, 1999

Attest:

Q. TODD DICKINSON

*Attesting Officer*     *Acting Commissioner of Patents and Trademarks*